United States Patent [19]

Yannopoulos

[11] Patent Number: 4,587,104
[45] Date of Patent: May 6, 1986

[54] SEMICONDUCTOR OXIDE GAS COMBUSTIBLES SENSOR

[75] Inventor: Lymperios N. Yannopoulos, Churchill Borough, Pa.

[73] Assignee: Westinghouse Electric Corp., Pittsburgh, Pa.

[21] Appl. No.: 564,051

[22] Filed: Dec. 21, 1983

[51] Int. Cl.⁴ ............................................. G01N 27/16
[52] U.S. Cl. ....................... 422/94; 73/27 R; 422/98; 436/134; 436/144
[58] Field of Search ............... 340/633, 634; 324/71.5; 73/27 R, 23; 422/94, 97, 98, 95, 90; 436/136, 137, 134, 143, 144, 151, 152

[56] References Cited

U.S. PATENT DOCUMENTS 4,259,292  3/1981  Ichinose et al. ................. 422/98
4,397,888  8/1983  Yannopoulos et al. ........... 427/86

FOREIGN PATENT DOCUMENTS 2826515  1/1979  Fed. Rep. of Germany ..... 73/27 R
54-9994   1/1979  Japan ................................. 422/98

Primary Examiner—Barry S. Richman
Assistant Examiner—Michael S. Gzybowski
Attorney, Agent, or Firm—Thomas R. Trempus

[57] ABSTRACT

An n-type semiconductor gas detecting element. The semiconductor oxide is bismuth molybdate having the composition $Bi_2O_3 \cdot 3MoO_3$ and the gas detecting element formed therewith has high sensitivity to combustible gas. The detection of the combustible gases is based upon the change of electrical conductivity of a thick film of the semiconductor oxide detecting element resulting from the combustible gas component in an oxygen-containing atmosphere.

3 Claims, 6 Drawing Figures

SEMICONDUCTOR OXIDE GAS COMBUSTIBLES SENSOR

BACKGROUND OF THE INVENTION

Field of the Invention

The invention relates to a thick film sensor for hydrogen and carbon monoxide and a method for preparing such a device. More particularly, the invention is a gas detecting element having a high degree of combustible gas sensitivity. The element is an n-type semiconductor oxide, bismuth molybdate, that does not require the presence of a catalyst.

There is a continuous need to detect pollutant gases and control the combustion efficiency in fuel burning chambers. This need has prompted the investigation of many combustible gas detection methods as well as the investigation of materials which can function as gas detecting elements in such methods. Recent advances in the field of heterogeneous catalyses have increased the interest in electronic sensing elements. Both n-type and p-type semiconductor oxide films are examples of electronic sensing elements which undergo measurable changes in their electronic conductivity, $\sigma$, on exposure to reducible gases in the presence of oxygen-containing atmospheres. The changes in $\sigma$ can be related to the concentration of combustible gases such as hydrogen and carbon monoxide and can be measured to determine concentration.

Heretofore, it has been the conventional belief that the conductivity changes in semiconductor oxide films became large enough to measure only if at least small amounts of a noble metal bearing compound catalyst are added to the semiconductor oxide film material. Stannic oxide has been found to be a particularly useful semiconductor oxide when it is mixed with small amounts of a noble metal catalyst such as platinum, palladium and rhodium. An example of an improved thick film stannic oxide sensor which is enhanced through the use of a selective catalyst is disclosed in U.S. Pat. No. 4,397,888, which is assigned to the present assignee and the contents of which are incorporated herein by reference.

It is therefore an object of this invention to provide an electronically active n-type semiconductor oxide material for the fabrication of a thick film gas sensing element.

It is another object of this invention to provide a gas sensor device for use in both pollution and gas boiler control applications.

It is a further object of this invention to provide an n-type semiconductor oxide material which does not require the presence of any catalyst for useful combustible gas response.

It is still another object of this invention to provide a sensor device characterized by fast, reproducible and reversible response to hydrogen and carbon monoxide as well as being characterized by ease and economy in manufacture.

SUMMARY OF THE INVENTION

The invention is an n-type semiconductor gas detecting element and a method for forming the same. The semiconductor oxide is bismuth molybdate having the composition $Bi_2O_3 \cdot 3MoO_3$ and the gas detecting element formed therewith has high sensitivity to combustible gas. The detection of the combustible gases is based upon the change of electrical conductivity of a thick film of the semiconductor oxide detecting element resulting from the combustible gas component in an oxygen-containing atmosphere.

BRIEF DESCRIPTION OF THE DRAWINGS

The above as well as other features and advantages of this invention will become apparent through consideration of the detailed description in connection with the accompanying drawings in which.

DESCRIPTION OF THE PREFERRED EMBODIMENTS

This invention is an improved gas detecting element having a high combustible gas sensitivity. A bismuth molybdate ($Bi_2O_3 \cdot 3MoO_3$) based semiconductor oxide gas detecting element has been found to display a measurable change in electrical conductivity in the presence of combustible gases, particularly carbon monoxide and/or hydrogen. These changes in electrical conductivity have been found to be reproducible and reversible.

Figure 1:
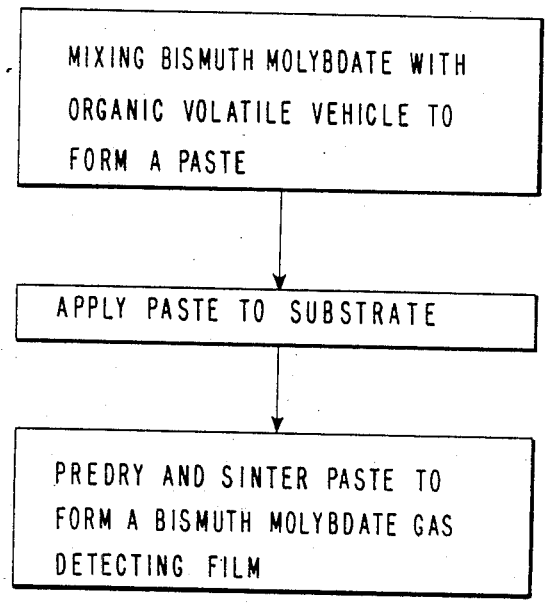
FIG. 1 is a diagram of the process steps for fabricating the improved semiconductor thick film sensor according to this invention.

A bismuth molybdate based thick film sensor according to this invention is fabricated according to the preparation process of FIG. 1. It has been found that the commercially available form of bismuth molybdate powder having a sieved size of about 43 μm or less is acceptable for use in the present process. It should also be noted that in, for example, gas boiler sensing applications, it is preferred that the gas sensing element be stable up to about 550° C. In the system $MoO_3$-$Bi_2O_3 \cdot 3MoO_3$, there is an eutectic at 618° C. The commercially available form of bismuth molybdate ($Bi_2O_3 \cdot 3MoO_3$) was tested up to approximately 550° C. in the gaseous environment of the gas boiler and was found to be stable.

Bismuth molybdate powder is mixed with an organic volatile vehicle such as Beta ($\beta$) terpineol to form a paste. The paste is then applied to a non-conductive and inert substrate to form a semiconductor oxide thick film. The pasted film is then pre-dried to less than about 100° C. and then slowly heated to a temperature less than the eutectic, preferably about 550° C. at which elevated temperature the pasted film is sintered for approximately two hours. The non-conductive and inert substrate can, for example, be a machinable lava of the silicate type onto which two platinum wire electrodes have been disposed. The paste is applied across the two electrodes so as to be in intimate electrical contact therewith.

Figure 2:
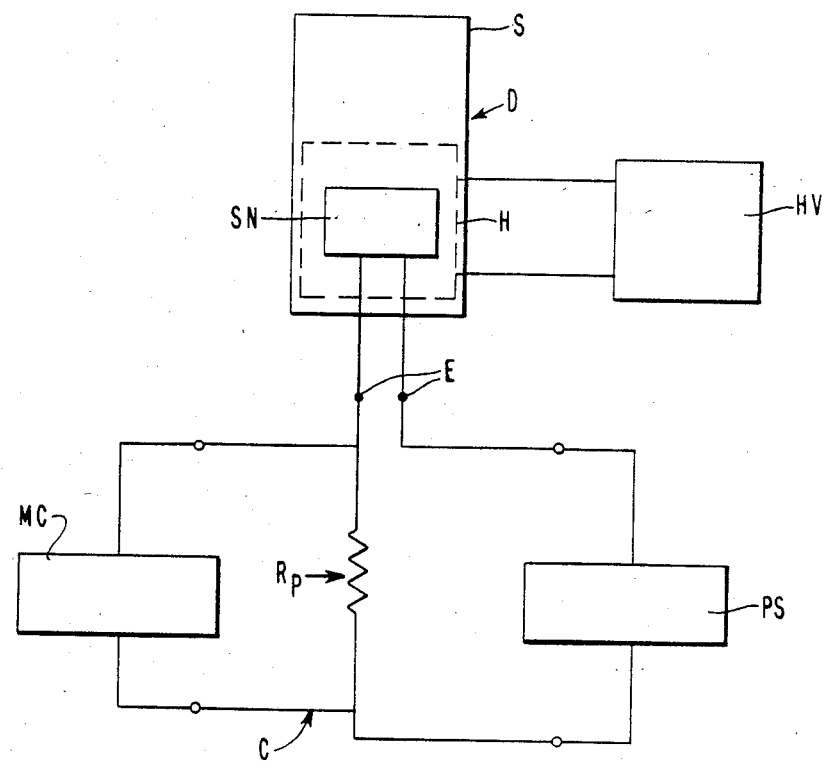
FIG. 2 is a schematic illustration of the application of the thick film sensor material of this invention as a device for the detection of combustibles.

Turning to FIG. 2, a typical application of a device D utilizing a semiconductor oxide combustibles gas sensor element of this invention is schematically represented. It is to be appreciated that the illustrated embodiment is an exemplar only, and that a variety of other substrate geometries and electrode configurations can be employed. The device D includes an inert and non-conductive substrate S onto which a pair of electrodes E are applied. A thick film of bismuth molybdate based sensor paste is applied to the surface of the substrate so as to effectively bridge the spaced-apart electrodes E. The oxide film sensor SN is in electrical communication with a measuring circuit MC which monitors the output of the sensor SN as a voltage across the standard resistor Rp of circuit C. This output is proportional to the resistance R of the device. The resistor Rp is connected in series with a DC power supply PS. The initial output value is predetermined in the absence of a fuel reducing gas mixture. On exposing the sensor SN of the gas measuring device D to a reducing gas mixture, the changes in output voltage as measured by the measuring circuit MC are related to the concentration of the fuel reducing constituents of the gas mixture. The operating temperature of the device can be achieved through the use of numerous heating techniques. However, a preferred technique is a film heater H which is a resistance film composition selection from the group consisting of $NiCo_2O_4$ and $PbRuO_3$ secured to the substrate S on the side thereof opposite the sensor SN and adapted to receive excitation from a heater voltage source HV. In applications where heat is provided by the test chamber, the heater voltage source can be eliminated.

The bismuth molybdate thick film sensor of this invention was tested for changes in its electrical resistance through exposure to varying concentrations of hydrogen or carbon monoxide in dry and water vapor-containing $O_2/N_2$ mixtures between 450° C. and 550° C. The response of the bismuth molybdate sensor element is shown in the table below:

| Reference Gas | Test Gas | Concentration Range (PPM) |
| --- | --- | --- |
| 0.5% $O_2/N_2$ | CO | 26.9–188 |
| 0.5% $O_2$/11% $H_2O/N_2$ | $H_2$ | 12–480 |
| 0.5% $O_2$/11% $H_2O/N_2$ | CO | 26.9–188 |

Figure 3:
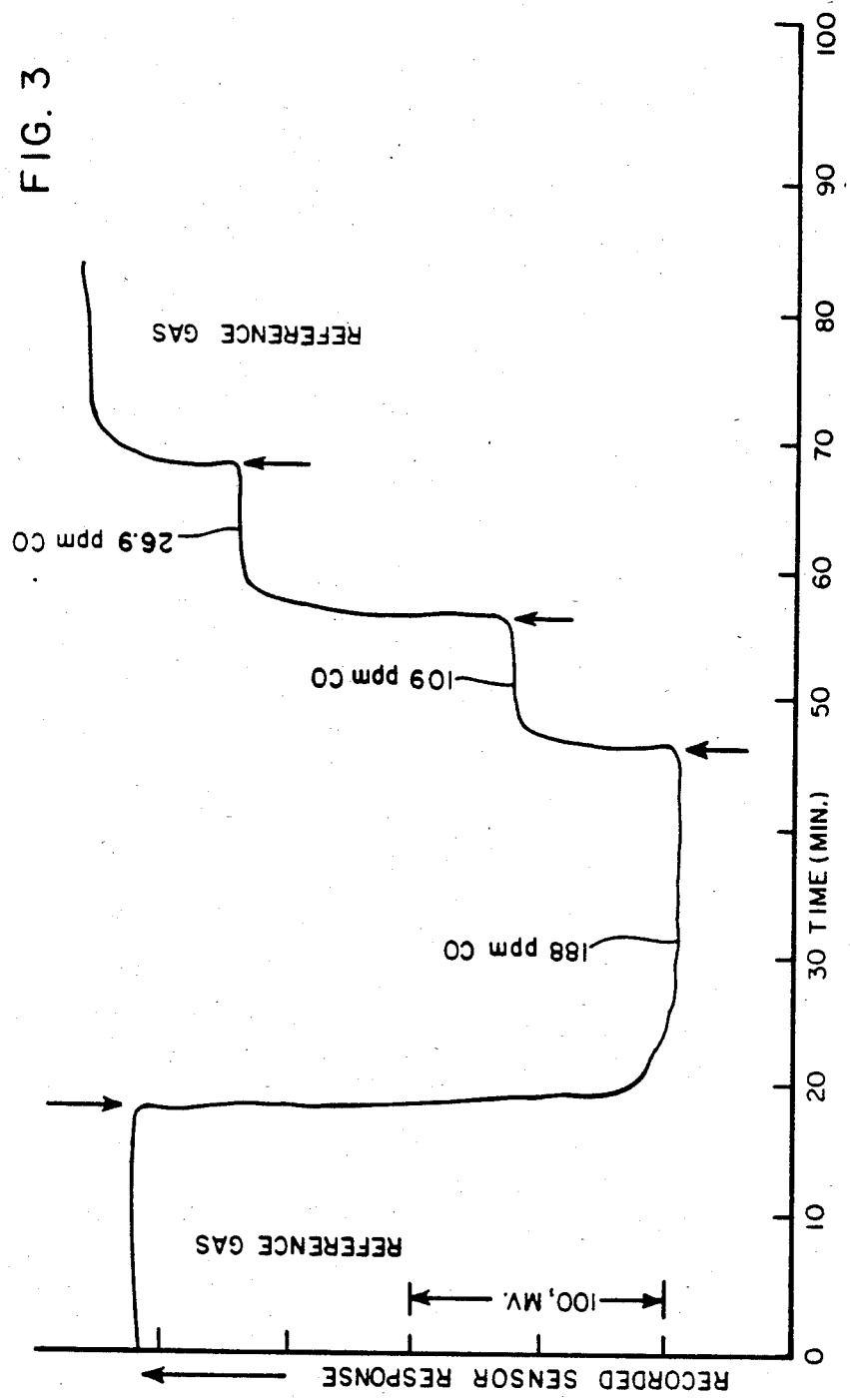
FIG. 3 is a trace of the recorded output of the $Bi_2O_3 \cdot 3MoO_3$ thick film sensor for CO in 0.5% $O_2/N_2$ reference gas.
Figure 4:
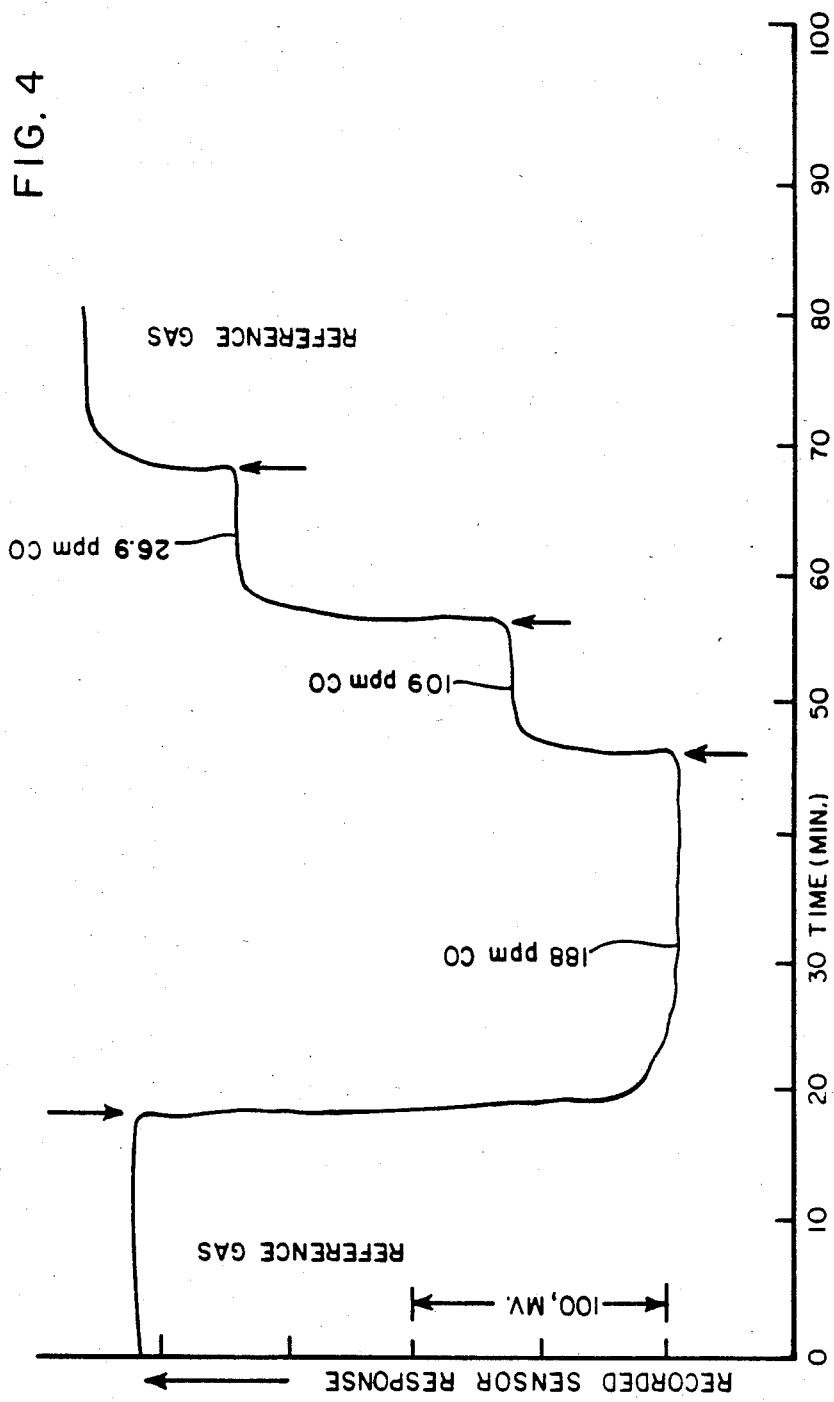
FIG. 4 is a trace of a recorded output of the $Bi_2O_3 \cdot 3MoO_3$ thick film sensor for CO in 0.5% $O_2/11\%$ $H_2O/N_2$.
Figure 5:
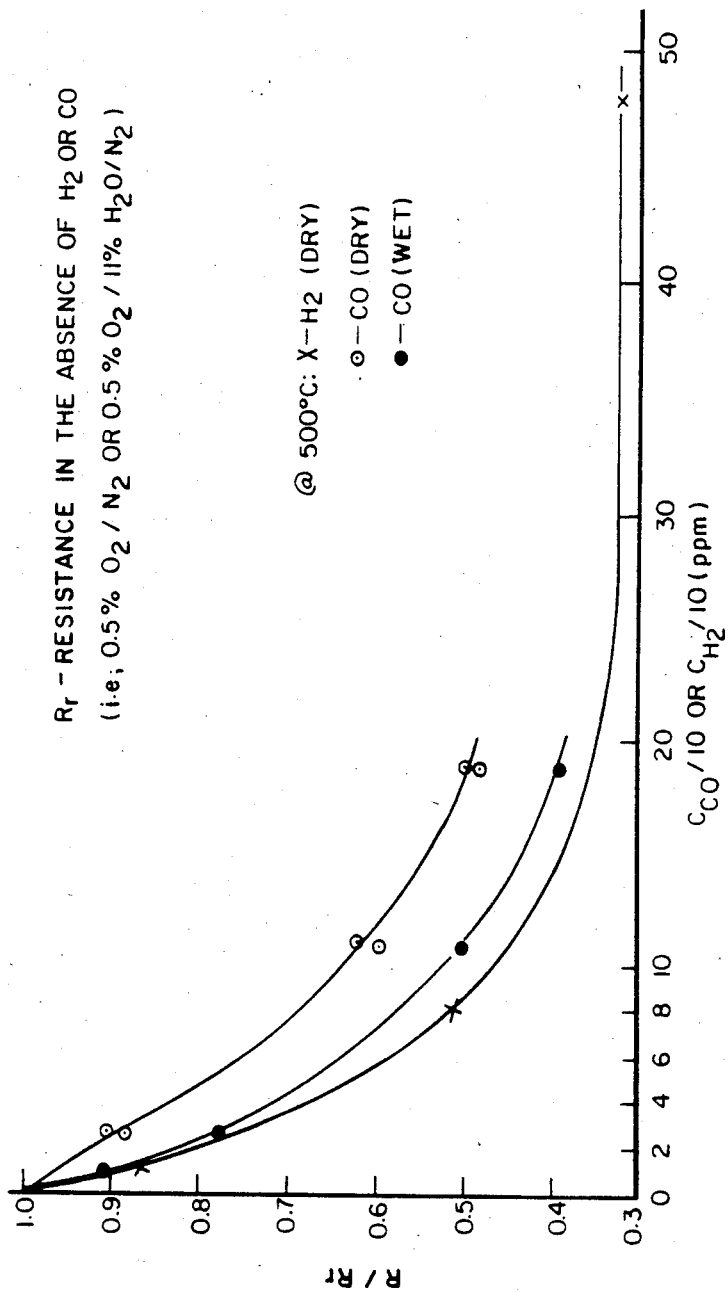
FIG. 5 is a graph representing the fractional change of the electrical resistance $(R/R_r)$ of $Bi_2O_3 \cdot 3MoO_3$-based thick film sensor versus concentration of CO or $H_2$ in 0.5% $O_2/N$ or 0.5% $O_2/11\%$ $H_2O/N_2$ at 500° C.
Figure 6:
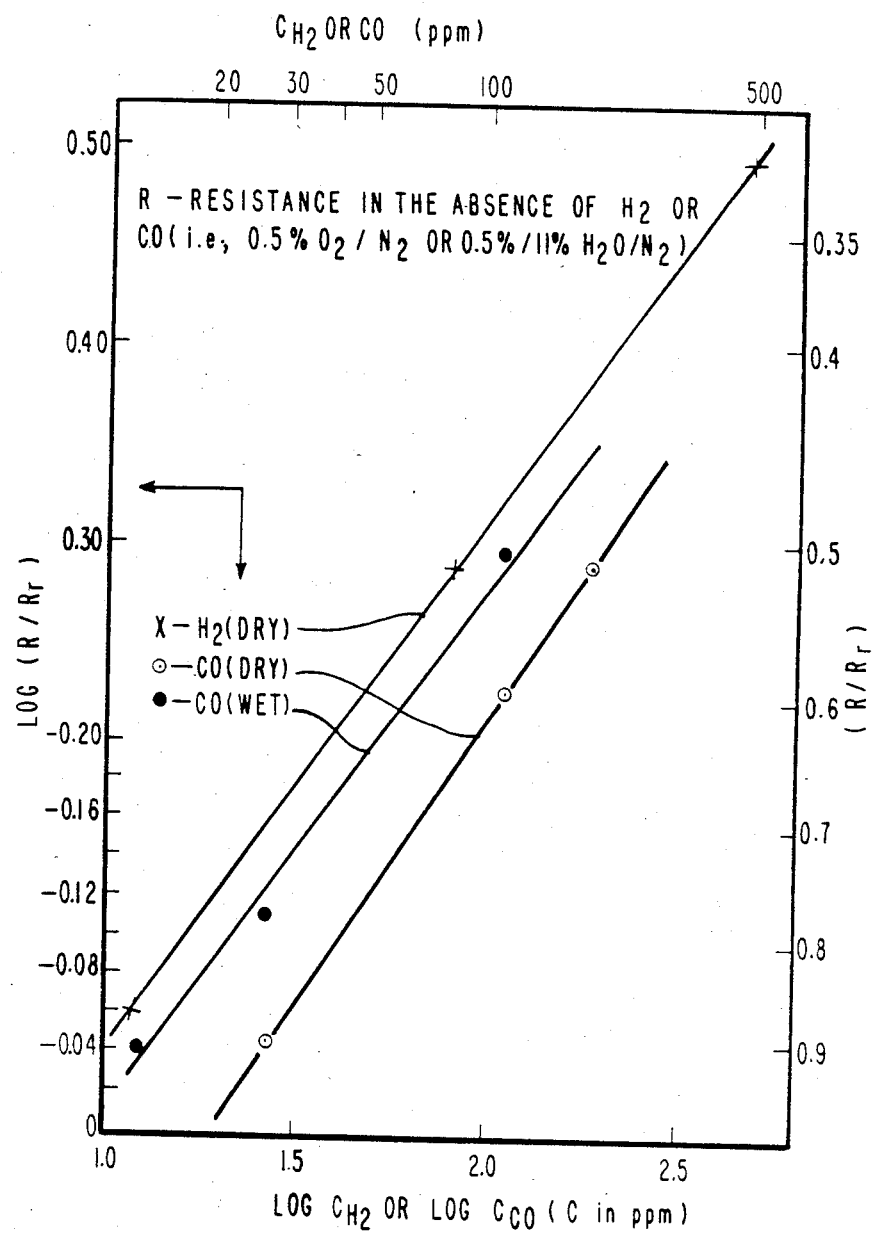
FIG. 6 is a graph representing the log-log plot of the $H_2$ or CO response of the $Bi_2O_3 \cdot 3MoO_3$-based thick film sensor in 0.5% $O_2/N_2$ or 0.5% $O_2/11\%$ $H_2O/N_2$ at 500° C.

In a typical test, the film support assembly is inserted in a quartz flow reactor tube. The electrical connections are made and the tube is heated to the desired temperature. The film is conditioned to a steady state resistance value under gas flow conditions. The gas reference mixtures are those given in the table. Those that contain the 11% $H_2O$ vapor simulate the water level expected in a typical gas ($CH_4$) burning boiler. The oxygen level used here (i.e., 0.5%) is also within the range of that found in such boilers. Once the steady state resistance value, $R_r$, is reached with the reference gas (0.5% $O_2/N_2$ or 0.5% $O_2$/11% $H_2O/N_2$), the combustible gas-doped mixture is switched on and the changes in the resistance are recorded as a function of time. The new steady state absolute value, R, is also recorded. The ratio, $R/R_r$, is taken as a measure of the combustible gas response of the thick film sensor. For the tested combustible gas concentration range given in the table (i.e., CO: 26.9-188 ppm; $H_2$: 12.0-480.0 ppm), the gas response data of the element is represented graphically in FIGS. 3 through 6. These figures show the exponential form of the combustible gas concentration dependence of the response, $R/R_r$, and its linearized form on a log-log scale. The typical time response (which is proportional to the resistance) is recorded and presented here for CO with the pure bismuth molybdate; the CO-response of this film with both the dry and wet 0.5% $O_2/N_2$ mixture is given in FIGS. 3 and 4, respectively.

The gas purge time with a chosen flow rate (650 cc/min) in the system was close to 30 seconds. The arrows in FIGS. 3 and 4 indicate the time of switching from one gas composition to the next. The traces clearly show that the CO response of the pure bismuth molybdate thick film is fast and useful for gas sensor applications. For example, within 30 seconds of the initial film sensor-gas contact, more than 70% of the resistance change is complete. The steady state (plateaus in FIGS. 3 and 4) is reached within about one and one-half minute. With regard to the magnitude of the resistance change, the pure bismuth molybdate film shows superior performance.

It has been found that the addition of hydroscopic molecular sieve powder (potassium aluminum silicate) is beneficial if the bismuth molybdate film sensors are to be used in environments where the temperatures are lower (i.e., 200° C.–350° C.) and water vapor present only as an impurity. In such an environment the hydrophilic additive will attract the water vapor molecules and the number of oxygen adsorbed sites will be essentially unaffected. It is this adsorbed oxygen that reacts with the combustible gas; it is related to its concentration, and also to the electrical resistance change caused by the charge transfer involved in such a reaction.

A more careful examination of the data of the tests reveals that the film response to $H_2$ is larger than that for CO in the dry 0.5% $O_2/N_2$ mixture. In the presence of water vapor, the response to CO is enhanced compared to that in the dry atmosphere. In fact this enhanced response to CO in the presence of water vapor becomes comparable to that of $H_2$ in the same atmosphere. In the presence of the hygroscopic additive, an identical $H_2$ and CO response is observed in the presence of water.

I claim:

1. A semiconductor oxide thick film fuel constituent detecting device responsive to the reaction of fuel and oxygen constituents in a monitored gas environment by exhibiting a change in electrical resistivity, which change is monitored as an indication of the fuel, or reducing, element in the monitored gas environment, comprising:

a non-conducting substrate member having upper and lower surfaces;

a pair of spaced-apart electrodes disposed on said substrate member;

a thick film semiconductor oxide element consisting of bismuth molybdate disposed in intimate contact with one of said surfaces of said substrate member and in intimate contact with said electrodes;

a film heater member disposed in intimate contact with the other of said surfaces of said substrate member electrical excitation means connected to said film heater means to heat said thick film element within a predetermined heating range; and circuit means for monitoring changes in resistivity of said thick film element in response to reactions of said fuel and oxygen constituents at the surface of said thick film element as an indication of the fuel constituent of the gas environment contacting said thick film element.

2. The device according to claim 1 wherein the film heater means is a resistance film composition selected from the group consisting of $NiCo_2O_4$ and $PbRuO_3$.

3. The device according to claim 1 wherein the pair of spaced-apart electrodes comprise platinum lead wires.

* * * * *